United States Patent
Doerr et al.

(10) Patent No.: US 11,707,627 B2
(45) Date of Patent: Jul. 25, 2023

(54) IMPLANTABLE MEDICAL DEVICE FOR STIMULATING A HUMAN OR ANIMAL HEART EMPLOYING AN AUTOMATIC CHOICE BETWEEN DIFFERENT IMPEDANCE MEASURING MODES

(71) Applicant: BIOTRONIK SE & Co. KG, Berlin (DE)

(72) Inventors: Thomas Doerr, Berlin (DE); Sergey Ershov, Berlin (DE); Torsten Radtke, Berlin (DE); Ulrich Busch, Berlin (DE); Peter Schneider, Berlin (DE); Frank Becker, Berlin (DE); Stefan Paule, Drosendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/769,911

(22) PCT Filed: Oct. 22, 2020

(86) PCT No.: PCT/EP2020/079730
§ 371 (c)(1),
(2) Date: Apr. 18, 2022

(87) PCT Pub. No.: WO2021/078846
PCT Pub. Date: Apr. 29, 2021

(65) Prior Publication Data
US 2022/0387797 A1    Dec. 8, 2022

(30) Foreign Application Priority Data
Oct. 24, 2019    (EP) ..................................... 19205046

(51) Int. Cl.
*A61N 1/365*    (2006.01)
*A61N 1/368*    (2006.01)
(Continued)

(52) U.S. Cl.
CPC ........ *A61N 1/36521* (2013.01); *A61B 5/0538* (2013.01); *A61N 1/056* (2013.01);
(Continued)

(58) Field of Classification Search
CPC .............. A61N 1/36521; A61N 1/3684; A61N 1/3686; A61N 1/3704
See application file for complete search history.

(56) References Cited

U.S. PATENT DOCUMENTS

| | | |
|---|---|---|
| 2019/0111265 A1 | 4/2019 | Zhou |
| 2019/0217097 A1 | 7/2019 | Thakur et al. |
| 2021/0016096 A1* | 1/2021 | Qiao ..................... A61N 1/3937 |

FOREIGN PATENT DOCUMENTS

EP    1234597 A2    8/2002

OTHER PUBLICATIONS

International Search Report (PCT/ISA/210) and Written Opinion (PCT/ISA/237) dated Jan. 21, 2021, by the European Patent Office as the International Searching Authority for International Application No. PCT/EP2020/079730.

* cited by examiner

*Primary Examiner* — George R Evanisko
(74) *Attorney, Agent, or Firm* — Buchanan Ingersoll & Rooney PC

(57)    ABSTRACT

An implantable medical device for stimulating a human/animal heart having a stimulation unit which stimulates the His bundle and a detection unit which detects an electrical signal at the His bundle. The device performs: a) determining a first value of a parameter of a first measuring pulse measured between a first electrode pole and a housing; b) determining a second value of the same parameter of a second measuring pulse measured between the first electrode pole and a second electrode pole; c) comparing the first and second values; d) determining, based on the comparing
(Continued)

step, whether the first or second measuring pulses enables a higher available level control range of the analog-to-digital converter; e) measuring an impedance in a unipolar manner between the first electrode pole and the housing or in a bipolar manner between the first electrode pole and the second electrode pole depending on the determining step.

14 Claims, 1 Drawing Sheet

(51) Int. Cl.
  *A61N 1/05*    (2006.01)
  *A61N 1/372*   (2006.01)
  *A61N 1/375*   (2006.01)
  *A61B 5/0538*   (2021.01)

(52) U.S. Cl.
  CPC ............ *A61N 1/365* (2013.01); *A61N 1/368* (2013.01); *A61N 1/3684* (2013.01); *A61N 1/36585* (2013.01); *A61N 1/3752* (2013.01); *A61N 1/37223* (2013.01); *A61N 1/37235* (2013.01); *A61N 1/37247* (2013.01); *A61N 1/37252* (2013.01)

IMPLANTABLE MEDICAL DEVICE FOR STIMULATING A HUMAN OR ANIMAL HEART EMPLOYING AN AUTOMATIC CHOICE BETWEEN DIFFERENT IMPEDANCE MEASURING MODES

CROSS-REFERENCE TO RELATED APPLICATIONS

This application is the U.S. National Phase under 35 U.S.C. § 371 of PCT International Patent Application No. PCT/EP2020/079730, filed on Oct. 22, 2020, which claims the benefit of European Patent Application No. 19205046.6, filed on Oct. 24, 2019, the disclosures of which are hereby incorporated by reference herein in their entireties.

TECHNICAL FIELD

The present invention relates to an implantable medical device for stimulating a human or is animal heart according to the preamble of claim 1, to a method for determining whether a cardiac impedance is to be measured in a unipolar manner or in a bipolar manner with such an implantable medical device according to the preamble of claim 12, and to a computer program product according to the preamble of claim 13.

BACKGROUND

Implantable medical devices for stimulating a human or animal heart, such as pacemakers, have been known for a long time. They can perform different functions. Different stimulation programs can be carried out by an appropriate pacemaker to restore the treated heart to a normal state. Pacemakers are also known to stimulate the His bundle.

The His bundle is a bundle of specific heart muscle cells that is part of the cardiac conduction system. The His bundle is located distally of the atrioventricular node towards the apex of the heart.

There exist specific devices adapted for His bundle pacing, wherein a detecting (sensing) and stimulation electrode is not implanted into the ventricle of the human or animal heart to be treated, but rather at or near to the His bundle of the heart. Such use of a His bundle electrode enables a particularly physiologic stimulation of the human or animal heart. However, the usual way to measure the impedance between an electrode implanted into an apical region of the right ventricle and a housing of the implantable medical device is no longer available in such a case. Nonetheless, the impedance is an important measure of the contractility of the treated heart so that it is also desired to measure the impedance with devices specifically adapted for His bundle pacing. In such devices, the impedance needs to be measured with the His bundle electrode. In doing so, different measuring modes, namely a unipolar measurement and a bipolar measurement are generally possible. Depending on the exact site of implantation and depending on physiological constraints, it might be advisable to apply either unipolar measurement or bipolar measurement.

The present disclosure is directed toward overcoming one or more of the above-mentioned problems, though not necessarily limited to embodiments that do.

SUMMARY

It is an object of the present invention to provide an implantable medical device for stimulating the His bundle of a human or animal heart that facilitates the choice of using the best measuring mode for determining the contractility of the heart.

At least this object is achieved with an implantable medical device for stimulating a human or animal heart having the features of claim 1. Such a device comprises a housing, an analog-to-digital converter, a processor, a memory unit, a stimulation unit and a detection unit. The stimulation unit is configured to stimulate the His bundle of the human or animal heart. The detection unit is configured to detect an electrical signal at the His bundle of the same heart. In this context, the detection unit comprises an electrode having a first electrode pole and a second electrode pole. In many instances, the stimulation unit makes use of the same electrode as the detection unit.

According to an aspect of the presently claimed invention, the memory unit comprises a computer-readable program that causes the processor to perform the steps explained in the following when executed on the processor.

In a first step, a first value of at least one parameter of a first measuring pulse is determined. In doing so, the first measuring pulse is measured between the first electrode pole and the housing of the implantable medical device.

In another step, a second value of the same at least one parameter of a second measuring pulse is determined. In this context, the second measuring pulse is measured between the first electrode pole and the second electrode pole.

Afterwards, the first value of the at least one parameter of the first measuring pulse and the second value of the at least one parameter of the second measuring pulse are compared with each other.

Within the frame of this application, a measuring pulse is understood as setting or changing at least one parameter for a certain amount of time (ranging from milliseconds to a couple of minutes) and measuring or determine the change or value of at least one parameter as a response.

Based on this comparison, it is determined whether the first measuring pulse or the second measuring pulse enables a higher available level control range of the analog-to-digital converter.

Afterwards, an impedance is measured in a unipolar manner between the first electrode pole and the housing of the implantable medical device if the first measuring pulse enables a higher available level control range of the analog-to-digital converter than the second measuring pulse. In contrast, an impedance is measured in a bipolar manner between the first electrode pole and the second electrode pole if the second measuring pulse enables a higher available level control range of the analog-to-digital converter than the first measuring pulse.

In choosing the measuring conditions enabling a higher available level control range of the analog-to-digital converter, the highest possible level control range of the analog-to-digital converter remains for the impedance measurement. This enables a reliable measurement of impedance signals even if the impedance signals decrease over time. Thus, this aspect of the presently claimed invention enables a particular appropriate use of the available electronic resources of the analog-to-digital converter depending on physiological frame conditions and the concrete site of implantation of the electrode serving as His bundle electrode. If there are high buffer resources in the level control range of the analog-to-digital converter, automatic gain control algorithms can be applied in a particular appropriate way to the detected signals in order to reliably detect impedance signals so as to be able to provide reliable data on the contractility of the human or animal heart to be treated.

An impedance change is typically an indicator of a length change of the heart since the impedance of blood is smaller than the impedance of muscle tissue. Thus, the longer the is conductivity pathway is established through blood, the lower is the impedance. The impedance is also an indicator of physical or mental stress of a patient. If a patient is under stress, the conductivity pathway of electrical signals in the heart is guided over a higher portion of muscle tissue than in case of a relaxed condition of the patient. Thus, the impedance in case of stress is higher than the impedance in case of a relaxed condition. This is due to the fact that the heart muscle is more contracted in a stressed state than in a relaxed state. Thus, the electrode tip typically comprising the electrode pole is surrounded in a stressed state to a higher extent by muscle tissue than in a relaxed state.

In an embodiment, the at least one parameter is chosen from the group consisting of an amplitude of the measuring current and measuring gain. Thus, if, e.g., an amplitude of the measuring current is determined for the first measuring pulse, it is necessary to also determine an amplitude of the measuring current of the second measuring pulse. Likewise, if a measuring gain of the first measuring pulse is determined, it is necessary to also determine the measuring gain of the second measuring pulse. It turned out that the measuring current and the measuring gain are particular appropriate parameters for determining the available level control range of the analog-to-digital converter of the implantable medical device. Preferably the measuring gain is determined by the measuring of the impedance and in particular the measuring of the change of the impedance over time. In addition, or as an alternative, the length of a current pulse and/or the number of current pulses per measuring pulse and/or the rate of the current pulses could be used as appropriate parameters for determining the available level control range.

Furthermore, it turned out that it is particularly appropriate to determine both the amplitude of measuring current and the measuring gain for the first measuring pulse and for the second measuring pulse to have particular reliable data on the available level control range of the analog-to-digital converter. Therefore, in an embodiment, both the amplitude of the measuring current and the measuring gain are determined. For such determination, it is possible, e.g., to measure the measuring current of the first measuring pulse and the second measuring pulse and to check a set measuring gain of the first and the second measuring pulse. Preferably the measuring of the measuring current, the impedance of the first measuring pulse to check the measuring gain of the first measuring pulse and the measuring of the measuring current and the measuring impedance to check the measuring gain of the second measuring pulse are done sequentially (preferably in a time frame of a several seconds to several minutes).

In an embodiment, the implantable medical device is an implantable pulse generator (IPG), an implantable cardioverter-defibrillator (ICD), or a device for cardiac resynchronization therapy (CRT).

In an embodiment, the computer-readable program causes the processor to classify the first value and the second value of the at least one parameter in a predefined class. This predefined class is one of a plurality of predefined classes. Each of the classes comprises a value range. The class being chosen for classifying the first value or the second value into it comprises a range that encompasses the respective value.

In doing so, it is possible to classify the first value and the second value into the same class or into different classes. A numeric index is assigned to each class. Consequently, the respective numeric index is also assigned to the value that is classified into this class. Thus, if, e.g., the index "3" is assigned to a specific class and if the first value is classified into this class, then the index "3" is assigned to the classified first value, too.

In an embodiment, the computer-readable program causes the processor to determine the values of at least two parameters, in particular exactly two parameters, of the first measuring pulse and the second measuring pulse and to classify the values into a predefined class comprising a value range that encompasses the respective value. Also in this case, a numeric index is assigned to each class. Since the values of at least two parameters (e.g., of 2, 3, 4, 5, or 6 parameters) are determined, more classes than in the precedingly explained embodiment are predefined. Then, a value of the first parameter is assigned to the class predefined for this first parameter, wherein a value of the second parameter is assigned to a class predefined for this second parameter.

In an embodiment, the numeric index increases with increasing values of the value range of the respective predefined class. Thus, comparatively lower indices are assigned to classes encompassing lower value ranges (like amplitude measuring current ranges or measuring is gain ranges) and comparatively higher indices are assigned to classes encompassing higher value ranges.

In an embodiment, the number of classes predefined for each parameter is a number falling in a range of from 2 to 20, in particular from 3 to 19, in particular from 4 to 18, in particular from 5 to 17, in particular from 6 to 16, in particular from 7 to 15, in particular from 8 to 14, in particular from 9 to 13, in particular from 10 to 12.

In an embodiment, the at least one parameter is the amplitude of the measuring current, wherein the predefined classes for the amplitude of the measuring current each encompass a range of from 10 µA to 1000 µA, in particular from 20 µA to 900 µA, in particular from 50 µA to 800 µA, in particular from 100 µA to 700 µA, in particular from 150 µA to 600 µA, in particular from 200 µA to 500 µA, in particular from 300 µA to 400 µA, in any desired distribution. To give an example, all classes may cover equally or non-equally broad amplitude ranges having a width falling in a range of from 10 µA to 200 µA, in particular from 20 µA to 150 µA, in particular from 30 µA to 125 µA, in particular from 40 µA to 100 µA, in particular from 50 µA to 90 µA, in particular from 60 µA to 80 µA. Particular appropriate widths cover an amplitude range of 25 µA, 50 µA, 75 µA, 100 µA, 125 µA, 150 µA, 175 µA, or 200 µA.

In an embodiment, the at least one parameter is the measuring gain. In this embodiment, the classes cover a gain range of from 2 to 200, in particular from 5 to 175, in particular from 8 to 150, in particular from 10 to 125, in particular from 12.5 to 110, in particular from 15 to 100, in particular from 20 to 90, in particular from 30 to 80, in particular from 40 to 70, in particular from 50 to 60. To give an example, all classes may cover equally or non-equally broad gain ranges having a width falling in a range of from 2 to 100, in particular from 3 to 80, in particular from 4 to 75, in particular from 5 to 70, in particular from 6 to 60, in particular from 7 to 50, in particular from 8 to 40, in particular from 9 to 30, in particular from 10 to 20.

In an embodiment, it is also possible to connect fixed measuring gain values with individual is classes. This embodiment is particularly appropriate if the gain cannot be adjusted and established manner. Particularly appropriate individual gain values start at the lowest value and are increased by a factor of the square root of 2.

If the values of more than one parameter are determined, it is possible that the same or a different amount of classes is predefined for the individual parameters.

In an embodiment, the computer-readable program causes the processor to accomplish the determining whether the first measuring pulse or the second measuring pulse enables a higher available level control range of the analog-to-digital converter by the steps explained in the following. If the value of exactly one parameter has been determined, it is determined whether the numeric index assigned to the single value of the at least one parameter of the first measuring pulse or the numeric index assigned to the single value of the at least one parameter of the second measuring pulse is lower. If, on the other hand, the values of more than one parameter have been determined, a first sum of the numeric indices assigned to all values of the at least one parameter of the first measuring pulse is calculated. Likewise, a second sum of the numeric indices assigned to all values of the at least one parameter of the second measuring pulse is calculated. Afterwards, it is determined whether the first sum or the second sum is lower. In a second step, it is determined that the first measuring pulse enables a higher available level control range of the analog-to-digital converter if the numeric index assigned to a single value of the at least one parameter of the first measuring pulse is lower than the numeric index assigned to a single value of the at least one parameter of the second measuring pulse (in case that the value of exactly one parameter has been previously determined). Alternatively, it is determined that the first measuring pulse enables a higher available level control range of the analog-to-digital converter if the first sum is lower than the second sum (in case that the values of more than one parameter have been previously determined). Likewise, it is determined that the second measuring pulse enables a higher available level control range of the analog-to-digital converter if the numeric index assigned to the single value of the at least one parameter of the second measuring pulse is lower than the numeric index assigned to the single value of the at least one parameter of the first measuring pulse (in case that the value of exactly one parameter has been previously determined). Alternatively, it is determined that the second measuring pulse enables a higher is available level control range of the analog-to-digital converter if the second sum is lower than the first sum (in case that the values of more than one parameter have been previously determined). Thus, either an individual numeric index is compared with another individual numeric index in case that only the value of one parameter has been determined. If, however, more than one parameter has been determined, the sum of the individual indices is calculated and afterwards compared with the sum of the respective indices for the other measuring pulse.

In an embodiment, the computer-readable program causes the processor to use the measured impedance as input value for adjusting at least one physical parameter of a stimulation pulse to be delivered by the stimulation unit to the His bundle of the heart. The adjustment of the physical parameter of the stimulation pulse can be achieved by algorithms already known per se. If such algorithms are fed with the impedance as input value, they are able to make patient-specific adjustments of the stimulation pulse to be subsequently delivered to the His bundle of the patient.

In an embodiment, the first electrode pole is located in a tip region (e.g., at the tip) of the electrode. Furthermore, the second electrode pole is located proximally of the tip region (i.e., located away from the tip region) of the electrode. In this context, the distance between the first electrode pole and the second electrode pole can be in a range of few millimeters to few centimeters, e.g., in a range of from 1 mm to 5 cm, in particular from 2 mm to 4 cm, in particular from 3 mm to 3 cm, in particular from 4 mm to 2 cm, in particular from 5 mm to 1.5 cm, in particular from 6 mm to 12 mm, in particular from 7 mm to 11 mm, in particular from 8 mm to 10 mm.

In an embodiment, the second electrode pole is realized in form of a ring electrode pole.

In an embodiment, the computer-readable program causes the processor to automatically adjust the measuring gain and to repeat steps a) to e) of claim 1, i.e., the steps of determining a first value, determining a second value, comparing the first value with the second value, determining which of the measuring pulses enables a higher available level control range of the analog-to-digital converter and to decide whether the impedance is to be measured in a is unipolar manner or in a bipolar manner.

In an embodiment, the computer-readable program causes the processor to measure the impedance using that measuring gain that resulted in the highest available level control range of the analog-to-digital converter. Thus, it is possible to consecutively check different measuring gains and to determine for each measurement the available level control range of the analog-to-digital converter and to subsequently choose the highest available level control range of the analog-to-digital converter. Thus, the consecutive execution of the individual method steps explained above under application of different measuring gains can result in the detection of an even higher available level control range of the analog-to-digital converter than in case of comparing only two individual measurements. Thus, increasing the number of test measurements can increase the probability of finding the best available measuring conditions for subsequent impedance measurements.

In an aspect, the present invention relates to a method for determining whether a (cardiac) impedance is to be measured in a unipolar manner or in a bipolar manner with an implantable medical device for stimulating a human or animal heart according to the preceding explanations. This method comprises the steps explained in the following.

In a first step, a first value of at least one parameter of a first measuring pulse is determined with a detection unit configured to detect an electrical signal at the His bundle of a human or animal heart. In doing so, the first measuring pulse is measured between a first electrode pole and a housing of the implantable medical device.

In another step, a second value of the same at least one parameter of a second measuring pulse is determined. In this context, the second measuring pulse is measured between the first electrode pole and a second electrode pole of the same electrode.

Afterwards, the first value of the at least one parameter of the first measuring pulse and the second value of the at least one parameter of the second measuring pulse are compared with each other.

Based on this comparison, it is determined whether the first measuring pulse or the second measuring pulse enables a higher available level control range of an analog-to-digital converter of the implantable medical device.

Afterwards, an impedance is measured in a unipolar manner between the first electrode pole and the housing of the implantable medical device if the first measuring pulse enables a higher available level control range of the analogto-digital converter than the second measuring pulse. In contrast, an impedance is measured in a bipolar manner between the first electrode pole and the second electrode pole if the second measuring pulse enables a higher available level control range of the analog-to-digital converter than the first measuring pulse.

In an aspect, the present invention relates to a computer program product comprising computer-readable code that causes the processor to perform the steps explained in the following when executed on the processor.

In a first step, a first value of at least one parameter of a first measuring pulse is determined with a detection unit configured to detect an electrical signal at the His bundle of a human or animal heart. In doing so, the first measuring pulse is measured between a first electrode pole and a housing of the implantable medical device.

In another step, a second value of the same at least one parameter of a second measuring pulse is determined. In this context, the second measuring pulse is measured between the first electrode pole and a second electrode pole of the same electrode.

Afterwards, the first value of the at least one parameter of the first measuring pulse and the second value of the at least one parameter of the second measuring pulse are compared with each other.

Based on this comparison, it is determined whether the first measuring pulse or the second measuring pulse enables a higher available level control range of an analog-to-digital converter of the implantable medical device.

Afterwards, an impedance is measured in a unipolar manner between the first electrode pole and the housing of the implantable medical device if the first measuring pulse enables a higher available level control range of the analog-to-digital converter than the second measuring pulse. In contrast, an impedance is measured in a bipolar manner between the first electrode pole and the second electrode pole if the second measuring pulse enables a higher available level control range of the analog-to-digital converter than the first measuring pulse.

In an aspect, the present invention relates to a medical method for treating a human or animal patient in need of such treatment by means of an implantable medical device for stimulating a human or animal heart, in particular by means of an implantable medical device according to the preceding explanations.

In a first step, a first value of at least one parameter of a first measuring pulse is determined with a detection unit configured to detect an electrical signal at the His bundle of a human or animal heart. In doing so, the first measuring pulse is measured between a first electrode pole and a housing of the implantable medical device.

In another step, a second value of the same at least one parameter of a second measuring pulse is determined. In this context, the second measuring pulse is measured between the first electrode pole and a second electrode pole of the same electrode.

Afterwards, the first value of the at least one parameter of the first measuring pulse and the second value of the at least one parameter of the second measuring pulse are compared with each other.

Based on this comparison, it is determined whether the first measuring pulse or the second measuring pulse enables a higher available level control range of an analog-to-digital converter of the implantable medical device.

Afterwards, an impedance is measured in a unipolar manner between the first electrode pole and the housing of the implantable medical device if the first measuring pulse enables a higher available level control range of the analog-to-digital converter than the second measuring pulse. In contrast, an impedance is measured in a bipolar manner between the first electrode pole and the second electrode pole if the second measuring pulse enables a higher available level control range of the analog-to-digital converter than the first measuring pulse.

Subsequently, the measured impedance is used as input value for adjusting at least one physical parameter of a stimulation pulse to be delivered by the stimulation unit to the His bundle of the heart of the patient.

Finally, the accordingly adjusted stimulation pulse is delivered to the His bundle of the patient's heart.

All embodiments of the implantable medical device can be combined in any desired way and can be transferred either individually or in any arbitrary combination to the described methods and the described computer program product. Likewise, all embodiments of the described methods can be combined in any desired way and can be transferred either individually or in any arbitrary combination to the respective other method, to the implantable medical device and to the computer program product. Finally, all embodiments described with respect to the computer program product can be combined in any desired way and can be transferred either individually or in any arbitrary combination to the described implantable medical device or to the described methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be described in the following making reference to exemplary embodiments and accompanying Figures. In the Figures.

DETAILED DESCRIPTION

Figure 1:
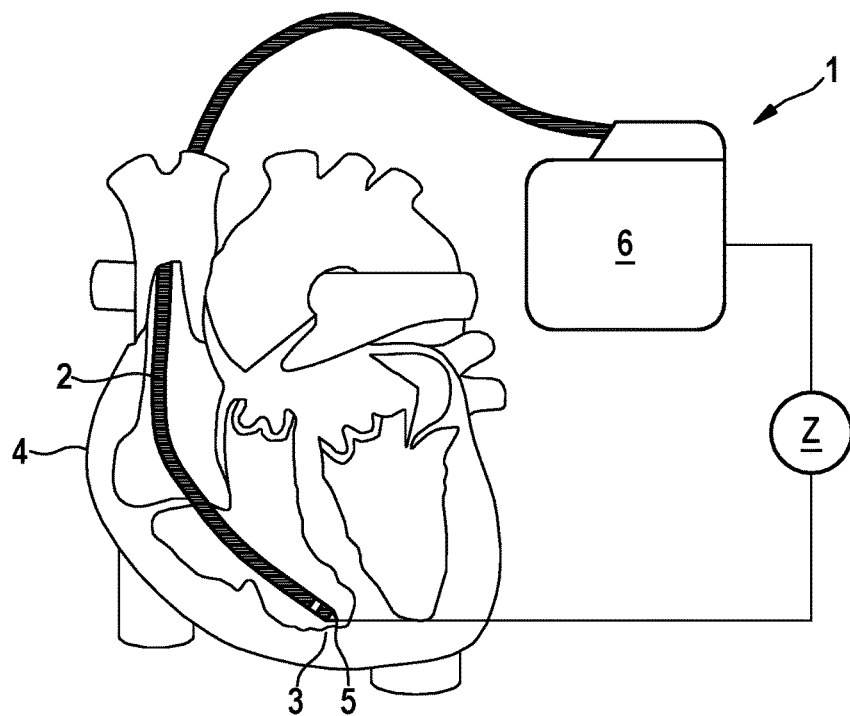
FIG. 1 shows a prior art setup for measuring an impedance in a unipolar manner.

FIG. 1 shows an implantable pulse generator 1 with a connected right ventricular electrode 2. This right ventricular electrode 2 is implanted in an apical region 3 of a human heart 4. The right ventricular electrode 2 comprises an electrode pole 5 at its tip. An impedance Z can be measured between the electrode pole 5 and a housing 6 of the implantable pulse generator 1 serving as counter electrode.

Figure 2:
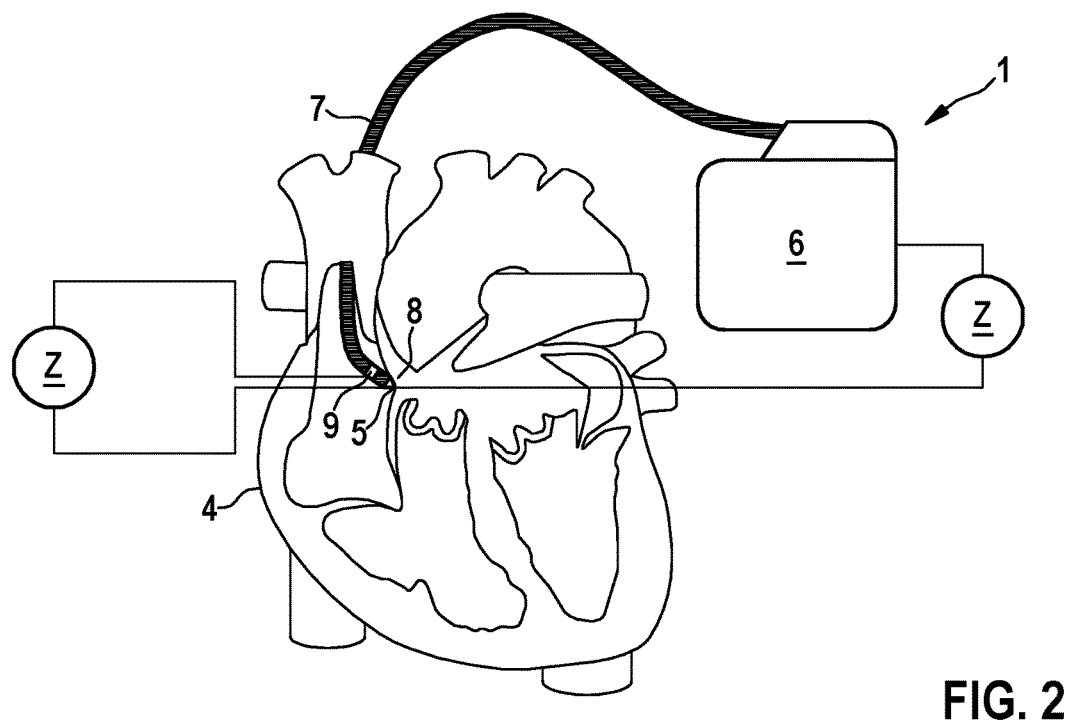
FIG. 2 shows two possible ways of measuring an impedance with a His bundle electrode.

FIG. 2 shows the situation in case of an implantable pulse generator 1 employing His bundle pacing as implantable medical device. Similar elements will be denoted with the same reference numerals as in FIG. 1.

In case of His bundle pacing, typically no right ventricular electrode is present. Rather, a His bundle electrode 7 is connected to the implantable pulse generator 1. The His bundle electrode 7 is implanted at the His bundle 8 of the human heart 4. A first electrode pole 5 contacts the cardiac tissue at or nearby the His bundle 8 so as to be able to stimulate the His bundle 8 of the human heart 4. A second electrode pole 9 is located proximally the first electrode pole 5.

It is now possible to measure an impedance in a unipolar manner between the first electrode pole 5 and a housing 6 of the implantable pulse generator 1. Such a measuring setup is similar to the measuring setup explained with respect to FIG. 1, but employs a different measuring path since the His bundle electrode 7 does not extend into the right ventricle of the human heart 4 as the right ventricular electrode 2 does (cf. FIG. 1).

Another possibility to measure the impedance is to apply a bipolar measurement between the first electrode pole 5 and the second electrode pole 9. In such a case, the measuring path is significantly shorter than in case of the unipolar measurement. Depending on the contractility of the human heart 4, a bipolar measurement may thus result in higher measuring currents than a unipolar measurement. However, this strongly depends on the concrete site of implantation of the His bundle electrode 7 in the cardiac tissue around the His bundle 8.

To decide whether a unipolar measurement or a bipolar measurement of the impedance is to be applied, a first measuring pulse is provided to the His bundle electrode 7, wherein both measuring gain and an amplitude of the measuring current are determined for this first measuring pulse. Subsequently, a second measuring pulse is applied to the His bundle electrode 7. Once again, the measuring gain and the amplitude of the measuring current are measured for this second measuring pulse. The first measuring pulse is applied between the first electrode pole 5 and the housing 6 of the implantable pulse generator 1, whereas the second measuring pulse is applied between the first electrode pole 5 and the second electrode pole 9.

In an exemplary experiment, the unipolar measurement of the first measuring pulse resulted in an amplitude of the measuring current amounting to 200 µA. Furthermore, the gain was determined to be 50.0. In case of the bipolar measurement of the second measuring pulse, the amplitude of the measuring current was higher, namely at 400 µA. At the same time, the measuring gain was determined to be only 18.8. These values of the parameters of the first measuring pulse and of the second measuring pulse were then classified with the help of the following Tables:

TABLE 1

Classes of amplitude ranges of measuring current.

| $Index_C$ | Amplitude of measuring current/µA |
|---|---|
| 0 | 0.1 to 50.0 |
| 1 | 50.1 to 100.0 |
| 2 | 100.1 to 200.0 |
| 3 | 200.1 to 300.0 |
| 4 | 300.1 to 400.0 |
| 5 | 400.1 to 500.0 |
| 6 | >500 |

TABLE 2

Classes of ranges of measuring gain.

| $Index_G$ | Measuring Gain |
|---|---|
| 0 | 0 to 6.0 |
| 1 | 6.1 to 10.0 |
| 2 | 10.1 to 15.0 |
| 3 | 15.1 to 20.0 |
| 4 | 20.1 to 30.0 |
| 5 | 30.1 to 45.0 |
| 6 | 45.1 to 60 |
| 7 | 60.1 to 75.0 |

TABLE 2-continued

Classes of ranges of measuring gain.

| $Index_G$ | Measuring Gain |
|---|---|
| 8 | 75.1 to 105.0 |
| 9 | >105.0 |

As can be seen from the preceding Table 1, each measuring current class covers a specific amplitude range of the measuring current and is assigned with a specific numeric index, called $index_C$. Likewise, as can be seen from the preceding Table 2, each individual class of the measuring gain covers a specific again range and is also assigned with a specific numeric index, called $index_G$.

The measuring results for the first measuring pulse (a current amplitude of 200 µA and a gain of 50.0) resulted in an assignment of $index_C=2$ and $index_G=6$ to the first measuring pulse. Likewise, the measuring results for the second measuring pulse (a current amplitude of 400 µA and a gain of 18.8) resulted in an assignment of $index_C=4$ and $index_G=3$ to the second measuring pulse.

Afterwards, $index_C$ and $index_G$ obtained for the first measuring pulse were added. Likewise, $index_C$ and $index_G$ obtained for the second measuring pulse were also added. The first sum for the first measuring pulse was 2+6=8. The second sum of the second measuring pulse 4+3=7.

A lower sum is the equivalent of a higher available level control range of the analog-to-digital converter of the implantable medical device.

Since 7 is lower than 8, a bipolar determination of the impedance was chosen as the method that enables a higher available level control range of the analog-to-digital converter of the implantable pulse generator 1. Therefore, subsequent impedance measurements were carried out by applying a bipolar determination of the impedance.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. Implantable medical device for stimulating a human or animal heart, comprising a housing, an analog-to-digital converter, a processor, a memory unit, a stimulation unit configured to stimulate the His bundle of a human or animal heart, and a detection unit configured to detect an electrical signal at the His bundle of the same heart, wherein the detection unit comprises an electrode having a first electrode pole and a second electrode pole, wherein the memory unit comprises a computer-readable program that causes the processor to perform the following steps when executed on the processor:

a) determining, by the detection unit, a first value of at least one parameter of a first measuring pulse generated by the stimulation unit, the first value measured between the first electrode pole and the housing;

b) determining, by the detection unit, a second value of the same at least one parameter of a second measuring pulse generated by the stimulation unit, the second value measured between the first electrode pole and the second electrode pole;

c) comparing the first value of the at least one parameter of the first measuring pulse to the second value of the at least one parameter of the second measuring pulse;

d) determining, based on the comparing of the preceding step, whether the first measuring pulse or the second measuring pulse enables a higher available level control range of the analog-to-digital converter;

e) measuring an impedance in a unipolar manner between the first electrode pole and the housing when the first measuring pulse enables a higher available level control range of the analog-to-digital converter than the second measuring pulse; and measuring an impedance in a bipolar manner between the first electrode pole and the second electrode pole when the second measuring pulse enables a higher available level control range of the analog-to-digital converter than the first measuring pulse.

2. Implantable medical device according to claim 1, wherein the at least one parameter is chosen from the group consisting of an amplitude of a measuring current of the first and second measuring pulses and a measuring gain of the first and second measuring pulses.

3. Implantable medical device according to claim 2, wherein both the amplitude of the measuring current and the measuring gain are used as the at least one parameter.

4. Implantable medical device according to claim 1, wherein the computer-readable program causes the processor to classify the first value and the second value of the at least one parameter into a predefined class comprising a value range encompassing the respective value, wherein a numeric index is assigned to each class.

5. Implantable medical device according to claim 4, wherein the numeric index increases with increasing values of the value range.

6. Implantable medical device according to claim 4, wherein the computer-readable program causes the processor to accomplish the determining whether the first measuring pulse or the second measuring pulse enables a higher available level control range of the analog-to-digital converter by the following steps: a) determining whether the numeric index assigned to a single value of the at least one parameter of the first measuring pulse or the numeric index assigned to a single value of the at least one parameter of the second measuring pulse is lower when the value of exactly one parameter of the at least one parameter has been determined; and a') calculating a first sum of numeric indices assigned to all values of the at least one parameter of the first measuring pulse and calculating a sum of numeric indices assigned to all values of the at least one parameter of the second measuring pulse when the values of more than one parameter of the at least one parameter have been determined and determining whether the first sum or the second sum is lower; and b) determining that the first measuring pulse enables a higher available level control range of the analog-to-digital converter when the numeric index assigned to a single value of the at least one parameter of the first measuring pulse is lower than the numeric index assigned to a single value of the at least one parameter of the second measuring pulse or when the first sum is lower than the second sum; and b') determining that the second measuring pulse enables a higher available level control range of the analog-to-digital converter when the numeric index assigned to a single value of the at least one parameter of the second measuring pulse is lower than the numeric index assigned to a single value of the at least one parameter of the first measuring pulse or when the second sum is lower than the first sum.

7. Implantable medical device according to claim 1, wherein the at least one parameter of the first and second measuring pulses comprises at least two parameters, and wherein the computer-readable program causes the processor to determine the values of the at least two parameters of the first measuring pulse and the second measuring pulse and to classify the values into a predefined class comprising a value range encompassing the respective value, wherein a numeric index is assigned to each class.

8. Implantable medical device according to claim 1, wherein the stimulation unit is configured to provide stimulation pulses to the human or animal heart, and wherein the computer-readable program causes the processor to use the measured impedance as input value for adjusting at least one physical parameter of a stimulation pulse to be delivered by the stimulation unit to the His bundle of the heart.

9. Implantable medical device according to claim 1, wherein the first electrode pole is located in a tip region of the electrode and in that the second electrode pole is located proximally of the tip region of the electrode.

10. Implantable medical device according to claim 1, wherein the computer-readable program causes the processor to adjust a measuring gain of the first and second measuring pulses and to repeat steps a) to e) of claim 1.

11. Implantable medical device according to claim 10, wherein the computer-readable program causes the processor to measure the impedance using the measuring gain that resulted in the highest available level control range of the analog-to-digital converter.

12. Method for determining whether a cardiac impedance is to be measured in a unipolar manner or in a bipolar manner with an implantable medical device for stimulating a human or animal heart, wherein the implantable medical device comprises a housing, an analog-to-digital converter, a processor, a memory unit, a stimulation unit configured to stimulate the His bundle of a human or animal heart, and a detection unit configured to detect an electrical signal at the His bundle of the same heart, wherein the detection unit comprises an electrode having a first electrode pole and a second electrode pole, the method comprising the following steps:

a) determining, with the detection unit configured to detect an electrical signal at the His bundle of the human or animal heart, a first value of at least one parameter of a first measuring pulse generated by the stimulation unit, the first value measured between first electrode pole of the electrode of the detection unit and the housing of the implantable medical device;

b) determining, with the detection unit, a second value of the same at least one parameter of a second measuring pulse generated by the stimulation unit, the second value measured between the first electrode pole and the second electrode pole of the same electrode;

c) comparing the first value of the at least one parameter of the first measuring pulse to the second value of the at least one parameter of the second measuring pulse;

d) determining, based on the comparing of the preceding step, whether the first measuring pulse or the second measuring pulse enables a higher available level control range of an analog-to-digital converter of the implantable medical device; and e) measuring an impedance in a unipolar manner between the first electrode pole and the housing when the first measuring pulse enables a higher available level control range of the analog-to-digital converter than the second measuring pulse; and measuring an impedance in a bipolar manner between the first electrode pole and the second electrode pole when the second measuring pulse enables a higher available level control range of the analog-to-digital converter than the first measuring pulse.

13. Computer program product comprising non-transitory computer-readable code that causes a processor to perform the following steps when executed on the processor:
 a) determining, with a detection unit configured to detect an electrical signal at the His bundle of a human or animal heart, a first value of at least one parameter of a first measuring pulse generated by a stimulation unit, the first value measured between a first electrode pole of an electrode of the detection unit and a housing of an implantable medical device for stimulating a human or animal heart;
 b) determining, with the detection unit, a second value of the same at least one parameter of a second measuring pulse generated by the stimulation unit, the second value measured between the first electrode pole and a second electrode pole of the same electrode;
 c) comparing the first value of the at least one parameter of the first measuring pulse to the second value of the at least one parameter of the second measuring pulse;
 d) determining, based on the comparing of the preceding step, whether the first measuring pulse or the second measuring pulse enables a higher available level control range of an analog-to-digital converter of the implantable medical device; and
 e) configuring the detection unit to measure an impedance in a unipolar manner between the first electrode pole and the housing when the first measuring pulse enables a higher available level control range of the analog-to-digital converter than the second measuring pulse; and configuring the detection unit to measure an impedance in a bipolar manner between the first electrode pole and the second electrode pole when the second measuring pulse enables a higher available level control range of the analog-to-digital converter than the first measuring pulse.

14. Method of treatment of a human or animal patient in need of such treatment by means of an implantable medical device for stimulating a human or animal heart, wherein the implantable medical device comprises a housing, an analog-to-digital converter, a processor, a memory unit, a stimulation unit configured to stimulate the His bundle of a human or animal heart, and a detection unit configured to detect an electrical signal at the His bundle of the same heart, wherein the detection unit comprises an electrode having a first electrode pole and a second electrode pole, the method comprising the following steps:
 a) determining, with the detection unit, a first value of at least one parameter of a first measuring pulse generated by the stimulation unit, the first value measured between the first electrode pole and the housing;
 b) determining, with the detection unit, a second value of the same at least one parameter of a second measuring pulse generated by the stimulation unit, the second value measured between the first electrode pole and the second electrode pole;
 c) comparing the first value of the at least one parameter of the first measuring pulse to the second value of the at least one parameter of the second measuring pulse;
 d) determining, based on the comparing of the preceding step, whether the first measuring pulse or the second measuring pulse enables a higher available level control range of the analog-to-digital converter;
 e) measuring an impedance in a unipolar manner between the first electrode pole and the housing when the first measuring pulse enables a higher available level control range of the analog-to-digital converter than the second measuring pulse; and measuring an impedance in a bipolar manner between the first electrode pole and the second electrode pole when the second measuring pulse enables a higher available level control range of the analog-to-digital converter than the first measuring pulse;
 f) using the impedance as input value for adjusting at least one physical parameter of a stimulation pulse to be delivered by the stimulation unit to the His bundle of the heart; and
 g) delivering the stimulation pulse to the His bundle of the heart.

* * * * *